United States Patent [19]
Bacich et al.

[11] Patent Number: 5,807,236
[45] Date of Patent: Sep. 15, 1998

[54] CATHETER WITH GUIDEWIRE AND ROUNDED ENLARGEMENT AND METHOD

[75] Inventors: Steven R. Bacich, Laguna Niguel; Tuoc Tan Nguyen, Westminster, both of Calif.

[73] Assignee: Imagyn Medical Inc., Laguna Niguel, Calif.

[21] Appl. No.: 630,121

[22] Filed: Apr. 8, 1996

Related U.S. Application Data

[63] Continuation-in-part of Ser. No. 238,314, May 5, 1994, Pat. No. 5,505,686.

[51] Int. Cl.$^6$ ........................................................ A61B 1/00
[52] U.S. Cl. ............................ 600/104; 600/114; 604/280
[58] Field of Search ...................... 600/104, 106, 600/114, 117, 103, 153, 156; 604/280, 164

[56] References Cited

U.S. PATENT DOCUMENTS

| | | |
|---|---|---|
| 3,941,121 | 3/1976 | Olinger et al. . |
| 4,254,762 | 3/1981 | Yoon . |
| 4,345,589 | 8/1982 | Hiltebrandt . |
| 4,345,602 | 8/1982 | Yoshimura et al. . |
| 4,449,532 | 5/1984 | Storz . |
| 4,538,622 | 9/1985 | Samson et al. . |
| 4,545,390 | 10/1985 | Leary . |
| 4,651,751 | 3/1987 | Swendson et al. . |
| 4,682,585 | 7/1987 | Hiltebrandt . |
| 4,762,129 | 8/1988 | Bonzel . |
| 4,773,394 | 9/1988 | Reichstein et al. . |
| 4,793,326 | 12/1988 | Shisido . |
| 4,798,193 | 1/1989 | Giesy et al. . |
| 4,807,593 | 2/1989 | Ito .......................................... 600/114 |
| 4,979,496 | 12/1990 | Komi . |
| 5,025,778 | 6/1991 | Silverstein et al. ...................... 600/104 |
| 5,197,457 | 3/1993 | Adair . |
| 5,207,213 | 5/1993 | Auhll et al. . |
| 5,251,611 | 10/1993 | Zehel et al. . |
| 5,279,280 | 1/1994 | Bacich et al. . |
| 5,292,305 | 3/1994 | Boudewijn et al. . |
| 5,300,023 | 4/1994 | Lowery et al. . |
| 5,337,733 | 8/1994 | Bauerfeind et al. . |
| 5,339,805 | 8/1994 | Parker . |
| 5,356,388 | 10/1994 | Sepetka et al. ...................... 600/280 X |
| 5,390,661 | 2/1995 | Griffith et al. . |
| 5,411,016 | 5/1995 | Kume et al. . |
| 5,490,845 | 2/1996 | Racz ...................................... 600/280 X |
| 5,527,298 | 6/1996 | Vance et al. ............................ 600/280 |

OTHER PUBLICATIONS

The Wilkerson Group, Inc., An Assessment of Percutaneous Transluminal Coronary Angioplasty and Its Impact on Related Cardiovascular Markets.

*Primary Examiner*—Beverly M. Flanagan
*Attorney, Agent, or Firm*—Donald E. Stout

[57] ABSTRACT

A catheter comprising an elongated catheter body having a distal end and an elongated flexible guidewire having proximal and distal ends. The guidewire includes a rounded enlargement between the ends of the guidewire. The guidewire is mounted on the catheter body for movement longitudinally relative to the catheter body between a first position in which the rounded enlargement is adjacent the distal end of the catheter body and a second position in which the rounded enlargement is located distally of the position the rounded enlargement occupies in the first position.

29 Claims, 3 Drawing Sheets

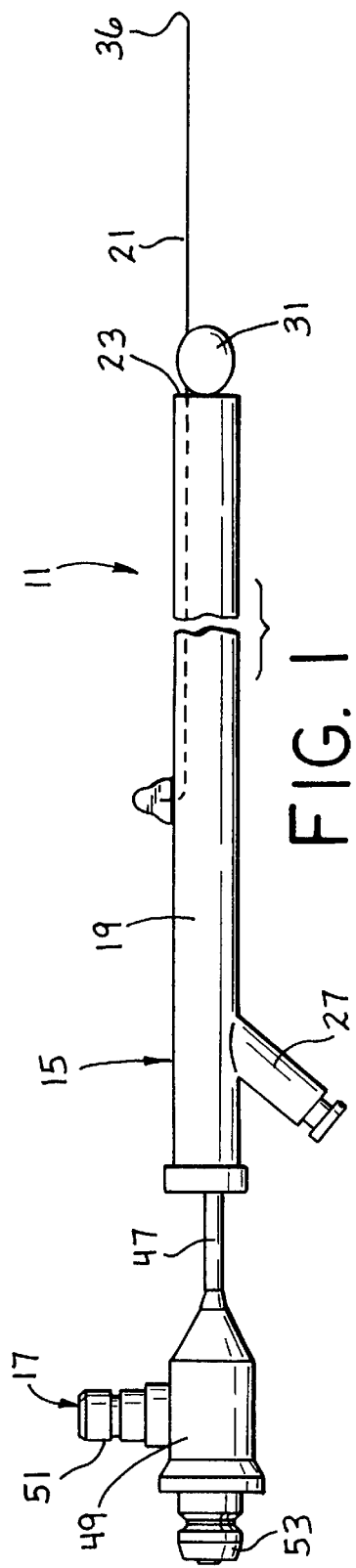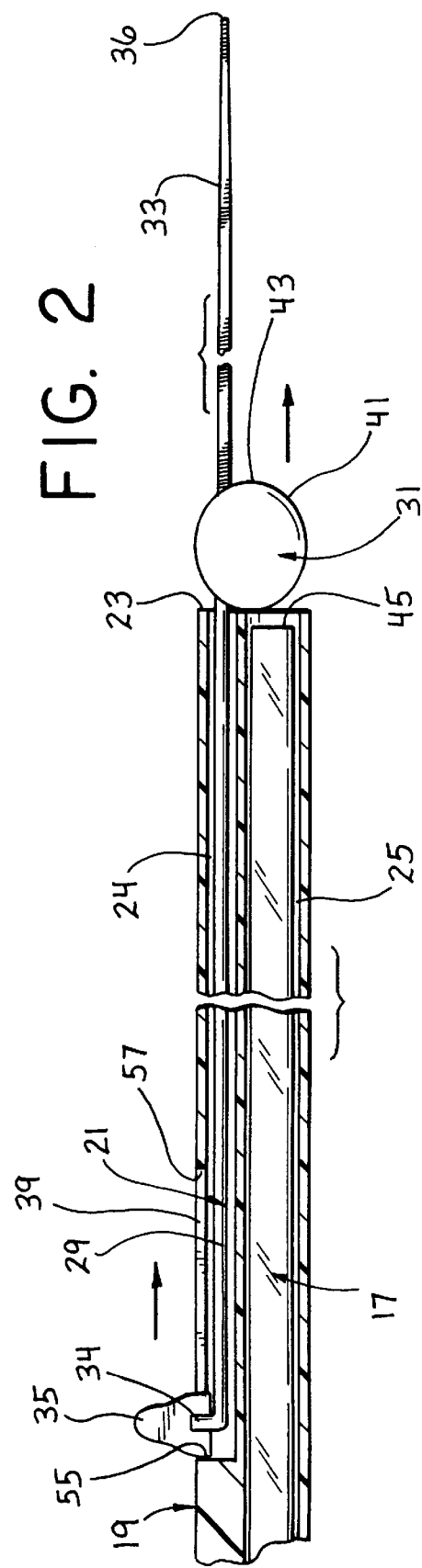

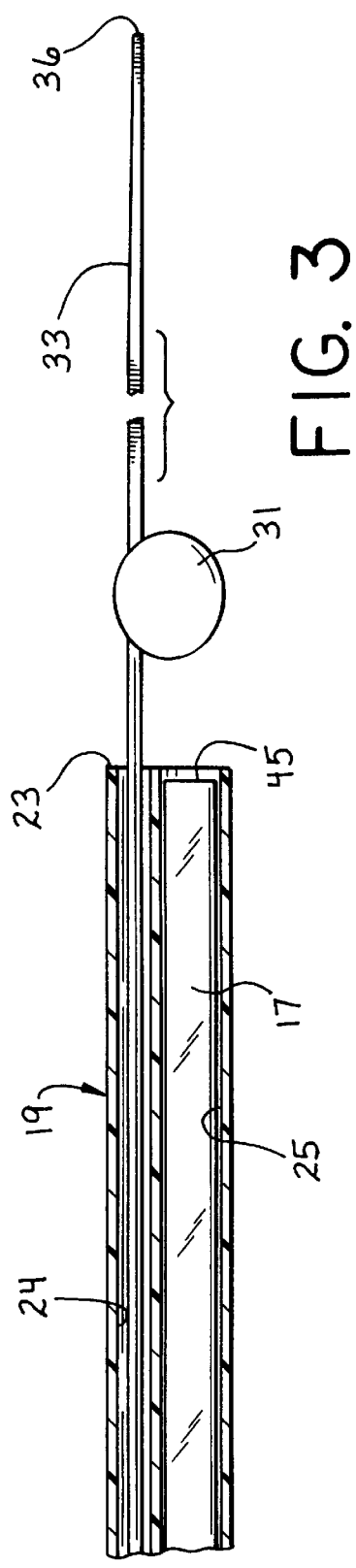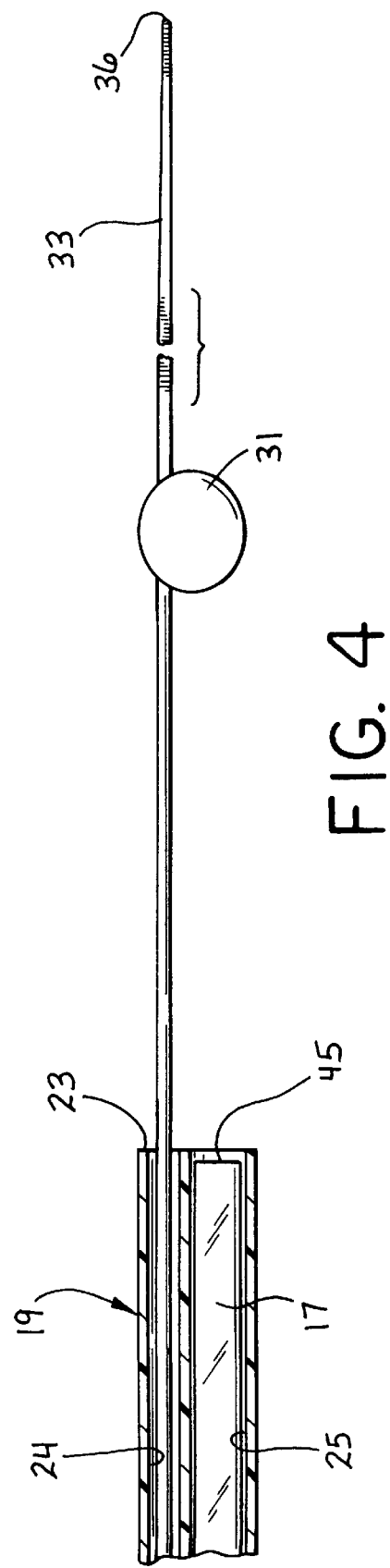

CATHETER WITH GUIDEWIRE AND ROUNDED ENLARGEMENT AND METHOD

CROSS REFERENCE TO RELATED APPLICATION

This application is a continuation-in-part of application Ser. No. 08/238,314 filed on May 5, 1994 and entitled Endoscope With Protruding Member and Method of Utilizing the Same now U.S. Pat. No. 5,505,686 and is also related to application Ser. No. 08/630,122, filed Apr. 8, 1996, and entitled CATHETER AND ENDOSCOPE SYSTEM WITH DISTAL PROTRUDING BALL TIP AND METHOD.

BACKGROUND OF THE INVENTION

Endoscopes are commonly used to view an interior passage of the body of a patient. For example, an endoscope may be used to view an interior passage such as a fallopian tube or a passage of the vascular system.

Various techniques can be used to place the endoscope at a desired location in the interior passage of the patient. For example, one such technique includes inserting a guidewire into the interior passage and running a catheter over the guidewire to approximately the desired location. With the catheter positioned in the interior passage, the guidewire may be withdrawn from the catheter and thereafter an endoscope inserted through a lumen of the catheter. Another known technique is to use a monorail system in which the endoscope is run along a prepositioned guidewire to a desired location in the interior passage. It is also known to provide an angioplasty catheter with a fixed guidewire which allows the operator to track and place the catheter at the desired location in the vascular system.

One problem with these procedures is that it may be difficult to view curved, collapsed or partially collapsed portions of the passage. In addition, material within the passage may tend to obstruct viewing through the endoscope within the field of view of the endoscope.

In an effort to solve this problem, it is known to use a resectoscope for removing or ablating unwanted tissue. It is also known to use a nozzle in an attempt to spray material off the distal lens of the endoscope as shown, for example in Auhll et al U.S. Pat. No. 5,207,213. However, these techniques do not address the visualization problems posed by a curved, collapsed or partially collapsed passage and resection increases the likelihood of injury and trauma to the patient. Similarly, the use of a technique as shown for example in Hiltebrandt U.S. Pat. No. 4,682,585 for radially spacing the distal objective of the endoscope is also not effective to address these problems.

Endoscopes have also been introduced through hollow sleeves with sharpened points for puncturing the abdomen in laparoscopic procedures such as shown in Hiltebrandt U.S. Pat. No. 4,345,589 and Yoon U.S. Pat. No. 4,254,762. However, the rigidity of the hollow sleeves and their sharp tips make them unsuited for many procedures where tissue penetration is to be avoided and for passages which are curved.

The invention of original application Ser. No. 08/238,314 now U.S. Pat. No. 5,505,686 solves these problems and enhances the viewing of the passage in which the endoscope is placed by relatively displacing the distal end of the endoscope and material within or forming the passage. According to the parent application, to accomplish the desired relative displacement the endoscope includes an elongated displacing member mounted on, and carried by, the endoscope body. This elongated displacing member can relatively displace the distal end of the endoscope body and material within the field of view of the endoscope to enhance viewing of the passage with the endoscope.

Companion application Ser. No. 08/630,122 filed on even date herewith and entitled Catheter and Endoscope System With Distal Protruding Ball Tip and Method discloses an invention in which it is the catheter, and not the endoscope, which carries the displacing member. One important advantage of having the displacing member carried by the catheter is that the relatively shorter useful life of the displacing member cannot reduce the longer useful life of the endoscope. Also, because the displacing member is relatively inexpensive, it does not add significantly to the cost of the disposable catheter.

SUMMARY OF THE INVENTION

This invention retains the advantages of the companion application while materially facilitating the advancing of the catheter in the interior passage of the patient. With this invention, the catheter includes a guidewire as an integral part of the catheter and the guidewire guides the advancing movement of the catheter in the interior passage of the patient. In addition, the guidewire includes a rounded enlargement which is useable to aid the advancing movement of the catheter in the interior passage and to aid viewing of the interior passage when an endoscope is placed within a lumen of the catheter.

A catheter useable with this invention may include an elongated catheter body having a distal end, a working or endoscope lumen and a guidewire lumen opening at the distal end. The catheter also includes an elongated flexible guidewire having proximal and distal ends, and the guidewire includes a rounded enlargement between the ends of the guidewire.

The guidewire is mounted on the catheter body for movement longitudinally relative to the catheter body from a first position in which the rounded enlargement is adjacent the distal end of the catheter body and a second position in which the rounded enlargement is located distally of the position the rounded enlargement occupies in the first position.

It is important to note that the guidewire is mounted on the catheter body, and therefore is an integral part of the catheter. Because the guidewire is part of the catheter and cannot be withdrawn, it always available for use with the catheter. By mounting the guidewire in a separate guidewire lumen in the catheter body, the endoscope can be advanced within the working lumen of the catheter without needing to be exchanged. The avoidance of exchanges saves time. This allows for endoscopic viewing at any time during the procedure and during the time of catheter advancement in the interior passage.

Because the guidewire is movable longitudinally relative to the catheter body, the rounded enlargement can be selectively positioned close to the distal end of the catheter body and distally of the distal end of the catheter body. This allows the rounded enlargement to provide, in effect, a rounded distal tip for the catheter body during the advancing of the guidewire and the catheter body in the interior passage of the patient. Once the catheter has reached the desired location, the guidewire and rounded enlargement can be relatively moved so as to place the rounded enlargement more distally of the distal end of the catheter body. In this position, the rounded enlargement can be used in the relative displacement of the distal end of the catheter body and material within or forming the passage within a zone of the interior passage so as to enhance viewing with an endoscope placed in the endoscope lumen.

The rounded enlargement is spaced proximally of the distal end of the guidewire. Preferably the rounded enlargement is spaced at least about 5 mm proximally of the distal end of the guidewire, and for some applications is spaced at least about 10 centimeters proximally of the distal end of the guidewire. Of course, spacings greater than 10 centimeters can be employed if desired. Although the guidewire could be mounted externally of the catheter body, it is preferred to provide the catheter body with the guidewire lumen and to mount the guidewire in the guidewire lumen. To facilitate moving of the guidewire longitudinally relative to the catheter body, the catheter preferably includes a controller carried by the catheter body. The working or endoscope lumen opens at the distal end of the catheter body and can receive an elongated endoscope or other medical instrument.

The distal section of the guidewire, i.e. the section from the rounded enlargement to the distal end of the guidewire may be of conventional guidewire construction, and as such may comprise, for example, an elongated wire coil having a rounded distal end. The distal section of the guidewire may have a length of from about 5 millimeters to about 10 centimeters.

According to the method of this invention, the guidewire and catheter body are placed into the interior passage of the patient. Next the guidewire and the catheter body are advanced in the interior passage of the patient with the guidewire guiding the advancing movement of the catheter body and with the rounded enlargement relatively close to the distal end of the catheter body to aid the advancing movement of the catheter body in the interior passage. The method includes relatively moving the guidewire and the catheter body to move the enlargement farther distally of the distal end of the catheter body following at least a portion of the step of advancing the catheter body. An endoscope is provided in the lumen of the catheter body and the distal end of the catheter body and material within or forming the passage within a zone of the interior passage is relatively displaced utilizing the enlargement. Then at least a portion of the zone of the interior passage can be viewed utilizing the endoscope while the distal end of the catheter body and the material are relatively displaced.

Various techniques can be used to provide the endoscope in the lumen of the catheter. For example, with the catheter body desirably placed in the interior passage, the endoscope may be subsequently advanced into the lumen relative to the catheter body. Alternatively, the endoscope may be inserted into the lumen of the catheter body prior to placement of the catheter body in the interior passage in which event the endoscope and catheter body are advanced together in the interior passage of the patient.

The relative displacement of the distal end of the catheter body and material in or forming the passage may open a collapsed or partially collapsed passage, displace the distal end of the catheter body from the wall of the passage, displace material within the passage that would otherwise obstruct the view and/or elongate a curved portion of the interior passage. The step of relatively displacing may include moving the catheter body relative to the endoscope. As to the view enhancing feature, the guidewire and enlargement may be moved longitudinally relative to the catheter body and/or the entire catheter and/or endoscope may be moved to achieve the desired view within the field of view of the endoscope.

The interior passage of the patient may be any of a variety of body passages. For example, the interior passage may be a fallopian tube, the gastrointestinal tract, a passage in the vascular system, a neural passage, an epidural passage or the urinary tract including the urethra and ureter.

A fluid such as a drug, a contrast dye or a gas such as $CO_2$ or an elongated medical instrument such as a probe (e.g. a cystology brush or pH probe) may be introduced through the working lumen of the catheter body to the interior passage whether or not the endoscope is in the lumen.

The guidewire is preferably resilient and the resilience allows it to be elastically deflected, and when the deflecting force is removed, its resilience, elasticity or memory will tend to return it to its original unstressed position. The region of the guidewire proximal of the enlargement, i.e. the proximal section, is preferably flexible in the sense that it can be elastically or resiliently deflected, but is not flexible in the sense of a length of string which has no memory for returning to its original position.

The enlargement of the resilient member provides a relatively wide area in radial cross section. For some applications it is preferred that the enlargement have a maximum cross-sectional area which is at least about as large as the cross-sectional area of the distal end of the catheter. For medical applications in the fallopian tube, the maximum cross-sectional dimension of the enlargement is preferably between about 0.15 mm and 1.2 mm.

The invention, together with additional features and advantages thereof may best be understood by reference to the following description taken in connection with the accompanying illustrative drawings.

BRIEF DESCRIPTION OF THE DRAWINGS

FIG. 1 is a side elevational view of an apparatus for viewing an interior passage of a patient.

FIG. 2 is an enlarged, fragmentary, longitudinal sectional view through the apparatus shown in FIG. 1.

FIG. 3 is a view similar to FIG. 2 with the guidewire and enlargement moved distally of the distal end of the catheter body.

FIG. 4 is a view similar to FIG. 2 with the guidewire and enlargement moved farther distally of the distal end of the catheter body.

DESCRIPTION OF THE PREFERRED EMBODIMENT

Figure 5:
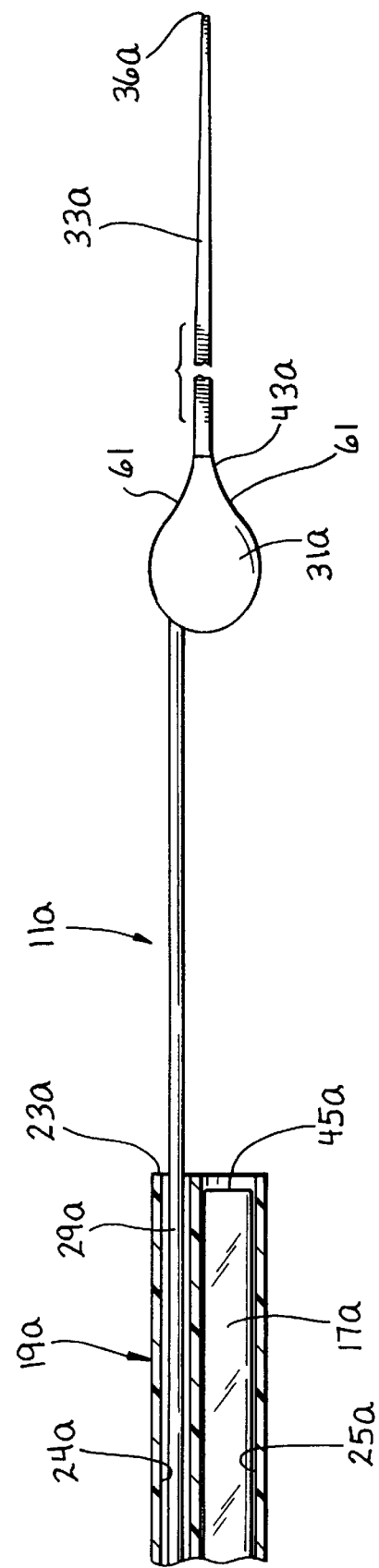
FIG. 5 is a view similar to FIG. 4 illustrating an alternate embodiment of the invention.

FIG. 1 shows an apparatus 11 constructed in accordance with the teachings of this invention which is useful in viewing an interior passage of a patient. The apparatus 11 generally includes a catheter 15 and an endoscope 17. The catheter 15 includes an elongated catheter body 19 (FIGS. 1 and 2) sized and adapted to be received in an interior passage of a patient and a guidewire 21. The catheter body 19 has a distal end 23, a guidewire lumen 24 (FIG. 2) and a working or endoscope lumen 25 extending for the full length of the catheter body and opening at the distal end. The guidewire 21 is mounted on and carried by the catheter body 19 and extends longitudinally beyond the distal end 23 of the catheter body.

The endoscope 17, which may be conventional, is positionable within the lumen 25 of the catheter body. The endoscope 17 is movable longitudinally within the lumen 25 relative to the catheter body 19 to a location for viewing a zone of the interior passage when the catheter body is within the interior passage.

The catheter 15, which is illustrated somewhat schematically in FIG. 1, also includes a leg 27 which communicates with the lumen 25 and which may be used, for example, for the infusion of a fluid. The catheter body 19, may be constructed of a suitable polymeric material. Although the catheter body 19 may be rigid, typically it will be flexible so it can conform to curvatures in the interior passage of the patient. Except for the guidewire 21 and its integration into the catheter body 19, the catheter 15 may be of conventional construction.

The guidewire 21 includes a proximal section 29 which is receivable in the guidewire lumen 24 as shown in FIG. 2, a bulbous or rounded enlargement 31 at the distal end of the proximal section and a distal section 33 attached to and projecting distally of the enlargement 31. The proximal section 29 may be in the form of a wire or a wire encased in a suitable lubricous sheath of nylon, Kinar or the like. The wire may be made of stainless steel or a suitable biocompatible polymeric material with sufficient flexural and column strength. In this embodiment, the proximal section 29 is constructed of a nickel-titanium alloy; however, other material may be used if desired. The elasticity of the proximal section 29 makes the proximal section highly flexible and easily deflected, but it will also enable the deflected proximal section to return to its natural or unstressed shape when the deflecting force is removed.

The proximal section 29 extends between a proximal end 34 of the guidewire 21 and the enlargement 31 and the distal section 33 extends between a distal end 36 of the guidewire and the enlargement. The proximal section 29 is slidable longitudinally in the guidewire lumen 24 relative to the catheter body 19. To enable this sliding movement to be manually controlled, a controller 35 is coupled to the proximal section 29 of the guidewire 21, and more specifically is attached to the proximal end 34 of the guidewire 21 (FIG. 2). The controller 25 slides in a longitudinally extending slot 39 in the catheter body 19. As shown in FIG. 2, the slot 39 communicates with the guidewire lumen 24. Consequently, the guidewire 21 is mounted on the catheter body 19 and is an integral part of the catheter 15 and by manually moving the controller 35 distally, the guidewire, including the rounded enlargement 31 are moved distally.

The enlargement 31 is preferably rounded so that it can be advanced through an interior passage of a patient with minimal trauma and without danger of perforation of the wall of the passage. The enlargement rounded 31 may be a member separate from the proximal section 29 and attached to the proximal section or it may be an integrally enlarged portion of the proximal section. The enlargement 31 has a smoothly rounded peripheral surface 41 which is blunt or non-penetrating both proximally and at a distal end 43 so as to minimize the likelihood of penetrating tissue when the catheter body 19 is advanced or retracted within an interior passage. For example, the rounded enlargement 31 may be generally egg-shaped as shown in FIG. 2, spherical, conical or a combination of these or other similar shapes and may be constructed of a polymeric material or a metal such as stainless steel or a nickel-titanium alloy.

The size of the enlargement 31 can be determined depending upon the interior passage which is to be viewed. Generally, however, the enlargement 31 has a maximum cross-sectional dimension in a radial plane of between about 0.15 and 1.2 mm and preferably between about 0.56 and 1.07 mm. For use in examination of a fallopian tube, the enlargement 41 preferably has a maximum cross-sectional dimension in a radial plane of about 0.6 mm. The enlargement is eccentrically mounted on the proximal section 29 so that it is generally axially aligned with the catheter body 19.

Generally, the proximal section 29 and the enlargement 31 have the necessary characteristics to contact material within or forming the interior passage of the patient and relatively displacing the distal end 23 of the catheter body 19 and such material to facilitate viewing of a zone of the interior passage with the endoscope 17. In addition, the proximal section 29 has sufficient column strength to permit it to be advanced to move the enlargement 31 and the distal section 33 distally of the position shown in FIG. 2.

The distal section 33 is suitably attached to the enlargement 31 and extends distally to the distal end 36 of the guidewire 21. The distal section 33 may be a conventional guidewire, and in the embodiment illustrated, is in the form of a wire coil having greater flexibility near the distal end 36 than adjacent the enlargement 31. The distal section 33 serves the usual guidewire function of guiding the advancing movement of the catheter body 19.

The endoscope 17 is preferably a fiberoptic endoscope having a distal end 45 and including an endoscope body 47 and a hub 49. The hub has a leg 51 which can be coupled to a light source (not shown) and a leg 53 which may be coupled to an eyepiece (not shown) to permit direct visualization or coupled to a camera (not shown) to enable an image to be viewed on a monitor. The endoscope 17 includes illumination fibers (not shown) which extend into the leg 51 and visualization or image fibers which extend into the leg 53 in a conventional manner.

The length of the slot 39 controls the amount to which the enlargement 31 can be moved distally from the position shown in FIG. 2. The opposite ends of the slot 39 provide proximal and distal stops 55 and 57 to define the maximum proximal and distal positions of the enlargement 31. The length of the slot 39 can be selected depending upon the use to which the catheter 15 is to be put. For example, the stops 55 and 57 may be spaced apart to enable the enlargement 31 to be advanced distally of the distal end 23 of the catheter body 19 a distance of from about 1 to about 15 mm. In this embodiment, the guidewire lumen 24 terminates proximally and provides the stop 55 for the controller 35 at a position at which the enlargement 31 is closely adjacent or in contact with the distal end 23 of the catheter body 19.

As an example of size, the catheter body 19 may have a diameter of between about 1.0 and 1.2 mm. The distal section 33 of the guidewire may be about 0.36 mm in diameter and the proximal section 29 may be about 0.2 mm in diameter. The endoscope body 47 may have a diameter of about 0.5 mm.

In use of the apparatus 11, the guidewire 21 and the catheter body 19 are placed into an interior passage of a patient. This is accomplished with the guidewire 21 in the proximal position of FIG. 2 in which the enlargement 31 is closely adjacent or in contact with the distal end 23 of the catheter body 19. Next, the guidewire 21 and the catheter body 19 are advanced in the interior passage of the patient with the guidewire guiding the advancing movement of the catheter body and with the enlargement being close enough to the distal end 23 of the catheter body 19 to give the catheter body a more rounded profile to thereby aid the advancing movement of the catheter body in the interior passage. The catheter body 19 and the guidewire 21 are preferably advanced simultaneously in the interior passage rather than sequentially.

The endoscope 17 is provided in the lumen 25 at any desired time which may be before, during or after the placement of the guidewire 21 and catheter 15 into the interior passage and the advancement of the catheter body 19 and the guidewire in the interior passage. If the endoscope is in the lumen 25 during the step of advancing, it can be used for viewing regions of the interior passage prior to the time the catheter body reaches its innermost position in the interior passage. In that event, it may be desirable to manually push the controller 35 distally of the position shown in FIG. 2 a small amount so as to displace the enlargement 31 distally of the distal end 23 of the catheter body 19 a short distance as shown in FIG. 3. This spaces the enlargement 31 from the distal end 45 of the endoscope 17 so that viewing of the interior passage is enhanced. Alternatively, the controller 35 may be used to retain the guidewire 21 in a static position and the catheter body can be moved slightly proximally to achieve the desired spacing between the enlargement 31 and the distal end 23 as shown in FIG. 3. Thus, all that is required is relative movement between the guidewire 21 and catheter body 19 so as to move the enlargement 31 farther distally of the distal end 23 of the catheter body 19. Of course, this relative movement may be carried out so as to displace the enlargement 31 a greater distance from the distal end 23 of the catheter body 19 as shown in FIG. 4.

In either the positions of FIGS. 3 or 4, the enlargement 31 may be used to displace the distal end 23 of the catheter body 19 and material within or forming the passage within a zone of the interior passage. This may be accomplished in a manner much like that described in parent application Ser. No. 08/238,314 which is incorporated by reference herein. For example, this relative displacement may occur as a result of contact between the material, such as a bend in the wall of the interior passage and the enlargement 31. However, this relative displacement can be accomplished in different ways and may include moving the catheter body 19 relative to the endoscope 17. At least some of the displacement of the material relative to the distal end 23 of the catheter body 19 is in a radial direction. The contact between the enlargement 31 and the material may occur during advancing and/or retracting of the catheter body 19 and/or while the catheter body is stationary within the interior passage.

This procedure has a number of advantages. For example, because of the enlarged and rounded nature of the enlargement 31 and because of its placement closely adjacent the distal end 23, the distal end 23 of the catheter body 19 is less likely to penetrate or damage tissue and the advancing movement of the catheter body in the interior passage is facilitated. When the enlargement 31 is moved distally to the positions of FIGS. 3 or 4, it can then serve the relative displacement function as to material within or forming the passage to enhance viewing with the endoscope 17.

FIG. 5 shows an apparatus 11a which is identical to the apparatus 11 in all respects not shown or described herein. Portions of the apparatus 11a corresponding to portions of the apparatus 11 are designated by corresponding reference numerals followed by the letter "a".

One difference between the apparatus 11a and the apparatus 11 is that in the apparatus 11a, the proximal section 29a and the distal section 33a are axially disaligned whereas in the apparatus 11 the proximal section 29 and the distal section 33 are axially aligned. More specifically, the distal section 33a is radially offset from the proximal section 29a so as to be in general axial alignment with the catheter body 19a. By axially aligning the distal section 33a and the catheter body 19a, the distal section may be better able to guide the advancing movement of the catheter body 19a.

A second difference between the apparatus 11a and the apparatus 11 is that the rounded enlargement 31a is generally tear drop shaped with the small end of the tear drop facing distally and with the longitudinal axis of the tear drop being generally coaxial with the catheter body 19a. The tear drop has generally concave surfaces 61 which smoothly blend the periphery of the enlargement 31a into the distal section 33a at the distal end 43a of the enlargement. The distal section 33a may be bonded or otherwise coupled to the enlargement 31a. The tear drop configuration of the enlargement 31a is preferably symmetrical about its longitudinal axis.

Although exemplary embodiments of the invention have been shown and described, many changes, modifications and substitutions may be made by one having ordinary skill in the art without necessarily departing from the spirit and scope of this invention.

We claim:

1. A catheter comprising:
    an elongated catheter body having a distal end;
    an elongated flexible guidewire having proximal and distal ends, said guidewire including a rounded enlargement between said ends of the guidewire;
    said guidewire being mounted on the catheter body for movement longitudinally relative to the catheter body from a first position in which the rounded enlargement is adjacent the distal end of the catheter body to a second position in which the rounded enlargement is located distally of the position the rounded enlargement occupies in the first position; and
    a controller carried by the catheter body for use in moving the guidewire longitudinally relative to the catheter body.

2. A catheter as defined in claim 1 wherein the rounded enlargement is spaced at least 5 mm proximally of the distal end of the guidewire.

3. A catheter as defined in claim 1 wherein the rounded enlargement is spaced at least 10 centimeters proximally of the distal end of the guidewire.

4. A catheter as defined in claim 1 wherein the catheter body has a guidewire lumen and the guidewire is at least partially received in the guidewire lumen.

5. A catheter as defined in claim 4 wherein the catheter body has a working lumen opening at the distal end of the catheter body for receiving a medical instrument or fluid.

6. A catheter as defined in claim 4 wherein the catheter body has a longitudinally extending slot communicating with the guidewire lumen, said controller is movable longitudinally in said slot and is coupled to the guidewire, and said slot has proximal and distal ends defining, respectively, proximal and distal stops for said controller.

7. An apparatus for viewing an interior passage of a patient comprising:
    an elongated catheter body having a distal end and working and guidewire lumens opening at the distal end;
    an elongated flexible guidewire having proximal and distal ends, said guidewire including a rounded enlargement between said ends of the guidewire;
    said guidewire being carried by the catheter body and being at least partially received in the guidewire lumen, said guidewire being movable longitudinally relative to the catheter body from a first position in which the rounded enlargement is adjacent the distal end of the catheter body and a second position in which the rounded enlargement is located distally of the position the rounded enlargement occupies in the first position; and an elongated endoscope in the working lumen.

8. A catheter as defined in claim 7 wherein the enlargement is spaced at least 5 mm proximally of the distal end of the guidewire.

9. A catheter as defined in claim 7 wherein the enlargement is spaced at least about 10 centimeters proximally of the distal end of the guidewire.

10. A catheter as defined in claim 7 including a controller carried by the catheter body for use in moving the guidewire longitudinally relative to the catheter body.

11. A method of viewing an interior passage of a patient using a catheter which includes a catheter body having a distal end, a lumen opening at the distal end and an elongated guidewire movable longitudinally relative to the catheter body and having a distal end and a rounded enlargement spaced proximally from the distal end of the guidewire, said method comprising:

placing the guidewire and catheter body into the interior passage in the patient;

advancing the guidewire and the catheter body in the interior passage of the patient with the guidewire guiding the advancing movement of the catheter body and with the enlargement relatively close to the distal end of the catheter body to aid the advancing movement of the catheter body in the interior passage;

relatively moving the guidewire and the catheter body to move the enlargement farther distally of the distal end of the catheter body following at least a portion of the step of advancing the catheter body;

providing an endoscope in the lumen of the catheter body;

relatively displacing the distal end of the catheter body and material within or forming the passage within a zone of the interior passage utilizing the enlargement; and viewing at least a portion of said zone of the interior passage utilizing the endoscope while the distal end of the catheter body and said material are relatively displaced.

12. A method as defined in claim 11 wherein the step of advancing includes advancing the catheter body and the guidewire simultaneously.

13. A method a defined in claim 11 wherein the step of providing is carried out before completion of the step of advancing.

14. A method as defined in claim 11 wherein the step of relatively displacing includes moving the catheter body relative to the endoscope.

15. A method as defined in claim 11 wherein the interior passage is a fallopian tube.

16. A method as defined in claim 11 wherein the interior passage is the gastrointestinal tract.

17. A method as defined in claim 11 wherein the interior passage is a passage in the vascular system.

18. A method as defined in claim 11 wherein the interior passage is a neural passage.

19. A method as defined in claim 11 wherein the interior passage is an epidural passage.

20. A method as defined in claim 11 wherein the interior passage is a passage in the urinary tract.

21. A method as defined in claim 11 including carrying out said step of providing before said step of advancing.

22. A method as defined in claim 11 including carrying out said step of providing after said step of advancing.

23. A catheter comprising:

an elongated catheter body having a distal end, a working lumen for receiving a medical instrument or a fluid and a guidewire lumen opening at the distal end of the catheter body;

an elongated flexible guidewire having proximal and distal ends, said guidewire including a rounded enlargement between said ends of the guidewire, a proximal section between the proximal end of the guidewire and the rounded enlargement and a distal section between the distal end of the guidewire and the rounded enlargement;

at least a portion of said proximal section of said guidewire being received in said guidewire lumen and mounted on the catheter body so that the guidewire can be moved longitudinally relative to the catheter body from a first position in which the rounded enlargement is adjacent the distal end of the catheter body to a second position in which the rounded enlargement is located distally of the position the rounded enlargement occupies in the first position and a controller carried by the catheter body and coupled to the proximal section of the guidewire for use in moving the guidewire longitudinally relative to the catheter body.

24. A catheter as defined in claim 23 wherein the catheter body has a longitudinally extending slot communicating with the guidewire lumen, said controller is movable longitudinally in said slot and is coupled to the proximal section of the guidewire, said slot has proximal and distal ends defining, respectively, proximal and distal stops for said controller, and wherein said controller engages the proximal stop when the enlargement is closely adjacent or in contact with the distal end of the catheter body.

25. A catheter as defined in claim 23 wherein the proximal and distal sections are axially aligned.

26. A catheter as defined in claim 23 wherein the proximal and distal sections are axially disaligned.

27. A catheter as defined in claim 23 wherein the rounded enlargement is generally tear drop shaped.

28. A catheter as defined in claim 23 wherein the rounded enlargement is blended smoothly into the distal section.

29. A catheter comprising:

an elongated catheter body having a distal end, a working lumen for receiving a medical instrument or a fluid and a guidewire lumen opening at the distal end of the catheter body;

an elongated flexible guidewire having proximal and distal ends, said guidewire including a rounded enlargement between said ends of the guidewire, a proximal section between the proximal end of the guidewire and the rounded enlargement and a distal section between the distal end of the guidewire and the rounded enlargement;

at least a portion of said proximal section of said guidewire being received in said guidewire lumen and mounted on the catheter body so that the guidewire can be moved longitudinally relative to the catheter body from a first position in which the rounded enlargement is adjacent the distal end of the catheter body to a second position in which the rounded enlargement is located distally of the position the rounded enlargement occupies in the first position; and the proximal and distal sections being axially disaligned.

* * * * *